United States Patent [19]
Moore, Jr.

[11] Patent Number: 5,865,143
[45] Date of Patent: Feb. 2, 1999

[54] HIGH-RISE LAYING HEN REARING FACILITY AND METHOD

[75] Inventor: Philip A. Moore, Jr., Fayetteville, Ark.

[73] Assignee: Trustees of University of Arkansas and United States of America

[21] Appl. No.: 735,103

[22] Filed: Oct. 22, 1996

Related U.S. Application Data

[60] Continuation-in-part of Ser. No. 437,991, May 10, 1995, Pat. No. 5,622,697, which is a division of Ser. No. 129,742, Sep. 30, 1993, abandoned.

[51] Int. Cl.$^6$ ............................. A01K 31/04; A01K 1/01
[52] U.S. Cl. ................... 119/442; 239/752; 239/209; 239/210; 239/99; 119/450; 119/458
[58] Field of Search ..................... 119/442, 443, 119/447, 450, 451, 458, 479, 448, 493, 518, 527, 163, 164, 162, 161; 239/752, 209, 210, 67, 99

[56] References Cited

U.S. PATENT DOCUMENTS

| | | | |
|---|---|---|---|
| 3,762,372 | 10/1973 | Mente et al. | 119/448 |
| 4,171,770 | 10/1979 | Mailander, Sr. | 237/3 |
| 4,208,279 | 6/1980 | Varani | 119/450 |
| 4,765,900 | 8/1988 | Schwoyer et al. | |
| 4,791,993 | 12/1988 | Curran | 239/209 |
| 5,136,980 | 8/1992 | Schoeber et al. | 119/161 |
| 5,148,771 | 9/1992 | Schuett et al. | 119/479 |
| 5,176,879 | 1/1993 | White et al. | |
| 5,289,912 | 3/1994 | Faulstich | 119/447 |
| 5,622,697 | 4/1997 | Moore, Jr. | 424/76.6 |

FOREIGN PATENT DOCUMENTS

| | | | |
|---|---|---|---|
| 80001 | 6/1983 | European Pat. Off. | 239/752 |
| 2905420 | 8/1980 | Germany | 119/450 |
| 1147302 | 3/1985 | U.S.S.R. | 119/527 |
| 15086 | 8/1900 | United Kingdom | 239/752 |

*Primary Examiner*—Todd E. Manahan
*Assistant Examiner*—Eduando C. Robert
*Attorney, Agent, or Firm*—Arthur J. Plantamura; Needle & Rosenberg, P.C.

[57] ABSTRACT

Atmospheric growing conditions in high-rise animal rearing facilities are improved by spraying liquid alum periodically over the manure collection area. Improved high rise animal rearing facilities provided with a liquid alum treatment delivery system for misting or spraying the liquid alum over the manure collection area to strip ammonia gas from the air and to apply a chemical coating on a surface of the accumulated manure which reduces or prevents ammonia volatilization. The liquid chemical treatment comprises an aqueous alum solution containing 1 to about 50% by weight alum, applied at a rate of about 50–250 g of $Al_2(SO_4)_3 \cdot 14H_2O$ per kg of manure as it accumulates. The improved rearing facilities and methods control the atmospheric conditions in the animal rearing area at less than or equal to about 25 ppm ammonia throughout the growing cycle.

8 Claims, 3 Drawing Sheets

HIGH-RISE LAYING HEN REARING FACILITY AND METHOD

CROSS REFERENCE TO RELATED APPLICATIONS

This application is a continuation-in-part of prior application Ser. No. 08/437,991, filed May 10, 1995 (now U.S. Pat. No. 5,622,697), which is a divisional of prior application Ser. No. 08/129,742, filed Sep. 30, 1993 (abandoned), the disclosures of which being hereby incorporated herein by reference.

BACKGROUND OF THE INVENTION

The present invention relates to new and improved odor-control system to enhance conditions in high-rise animal rearing facilities. More particularly, it relates to apparatus and methods that employ alum to control the chemical composition of the atmosphere in the animal rearing levels of a high-rise rearing facility.

One of the predominant systems currently used for egg production from laying hens involves growing the birds in cages on the second floor of a two story animal rearing facility referred to as a high-rise laying hen house. In these houses, the manure from the birds falls from the second floor to the first floor where it accumulates. After a period of time, the manure is removed from the house and applied to the land as an agricultural fertilizer.

Accumulation of manure in animal rearing facilities results in the production of ammonia gas, which can be produced in relatively high quantities. For over thirty years, researchers have known that buildup of ammonia levels in animal rearing facilities adversely affects poultry and other animals. Research on the effects of ammonia on poultry has shown that it causes decreased growth rates, reduced feed efficiency, decreased egg production, damage to the respiratory tract, increased susceptibility to New castle disease, increased incidence of airsaculitis, increased levels of *Mycoplasma gallisepticum*, and increased incidence of keratoconjunctivitis. For these reasons, it is now recommended that 25 ppm ammonia should not be exceeded in poultry houses.

Ammonia volatilization from poultry litter has also been shown to be detrimental to the environment due to its effect on acid atmospheric deposition. Ammonia plays a key role in acid rain production and the dominant source of atmospheric ammonia in Europe was found to be livestock wastes, with long-term trends showing a 50% increase in ammonia emissions in Europe from 1950–1980. Ammonia raises the PH of rainwater, which allows more $SO_2$ to dissolve in it, eventually forming ammonium sulfate, which releases nitric and sulfuric acid in soils upon oxidation. Ammonia volatilization also greatly increases atmospheric N fallout, which contributes to eutrophication. N deposition from wet fallout tripled from 1955 to 1980 and corresponded with N losses from agriculture during this same period. Atmospheric ammonia can also result in the formation of ammonium nitrate particles in the air. These particles, which are usually less than two microns in size, contribute greatly to small airborne particle pollution referred to as $PM_{10}$'s (particulate matter less than 10 microns).

Another environmental problem currently facing the poultry industry is phosphorus runoff from fields receiving poultry manure as an agricultural fertilizer. Phosphorus is considered to be the primary element of concern with respect to eutrophication of fresh water systems. Recent studies have shown extremely high phosphorus concentrations in the runoff water from pastures receiving low to moderate levels of poultry manure as fertilizer. The majority (80–90%) of the phosphorus in the runoff water is dissolved reactive P, which is the form that is more readily available for algal uptake. The threat of eutrophication due to phosphorus runoff has results in limits being placed on the number of animals which may be produced per area of land in the Netherlands.

Similar problems are encountered with manure deposited in other facilities in which other animals, such as poultry breeding stock, are reared in a raised facility.

Accordingly, new facilities and methods are needed for rearing animals under conditions which reduce ammonia volatilization, prevent nitrogen losses to improve the fertilizer value of manure to be used as an agricultural fertilizer and to reduce the soluble phosphorus content of the manure to prevent phosphorus runoff from fields fertilized with poultry manure agricultural fertilizers.

SUMMARY OF THE INVENTION

In accordance with these and other objects, the present invention, in an embodiment, provides a new and improved animal rearing facility. The animal rearing facility comprises an animal enclosure including a raised animal rearing platform. The rearing platform is disposed in the enclosure and divides the enclosure to define an upper animal rearing area above the platform and a lower manure collection area below the platform and the animal rearing area. The platform has a plurality of openings defined therein permitting manure produced in the animal rearing area to fall through the platform to the manure collection area. The animal rearing facility further comprises at least one sprayer nozzle disposed in the manure collection area adjacent an underside surface of the platform. A supply of liquid chemical treatment is provided which is fluidly connected with the sprayer nozzle or nozzles. The new and improved animal rearing facility further comprises means for delivering liquid alum from the supply to the sprayer nozzle under pressure.

The new and improved animal rearing facility preferably sprays the liquid alum solution through the sprayer nozzles for spraying time periods and at spraying intervals which are effective to strip the air of any ammonia gas that is present and to deposit a layer of alum on the surface of the manure in the manure collection area to prevent volatilization of ammonia from the collected manure. This reduces the concentration of ammonia gas in the upper animal rearing level of the facility to provide improved growing conditions for the animals reared therein. The alum treatments also increase the nitrogen content of the manure by preventing ammonia losses and reduce the quantity of soluble phosphorus present in the manure making the manure more useful as an agricultural fertilizer.

The present invention also provides a definite improvement in enhancing the environment above the manure collection level during the growth cycle of livestock, especially chickens and turkeys, raised in the enclosure. This is effected by periodically spraying a liquid alum solution onto the manure collection level in an amount sufficient to provide a treated or coated surface on the accumulated manure which maintains the pH of the surface of the manure at a pH of about 7.0 or lower. The liquid alum solution is sprayed onto an upper surface of the manure in amounts and at spraying intervals which are effective to maintain the pH of the surface of the manure at less than or equal to about 7.0. In addition, the liquid alum solution is sprayed in amounts and at spraying intervals which are effective to control the atmospheric concentration of ammonia in the animal rearing level at less than or equal to about 25 ppm.

A major advantage provided by the new and improved facilities and methods of the present invention is that improved growth rates, improved feed efficiency, improved increased egg production, better weight gain and a decrease in the incidence of disease may be provided to laying hens grown in a high-rise animal rearing facility.

Another advantage provided by the apparatus and the methods of the invention is that the nutrient or nitrogen value of the animal manure is enhanced, improving its quality as an agricultural fertilizer.

Another advantage provided by the present invention is that it provides an improved control of odors associated with animal manures.

Still another advantage provided the present invention is that it provides reduced ammonia volatilization from poultry or animal manures so that the detrimental impact occasioned by the use of the manures as agricultural fertilizers on acid atmospheric deposition is reduced.

Other objects and advantages of the present invention will become apparent from the following detailed description taken in conjunction with the drawings in which.

DETAILED DESCRIPTION OF THE PREFERRED EMBODIMENTS

Figure 1:
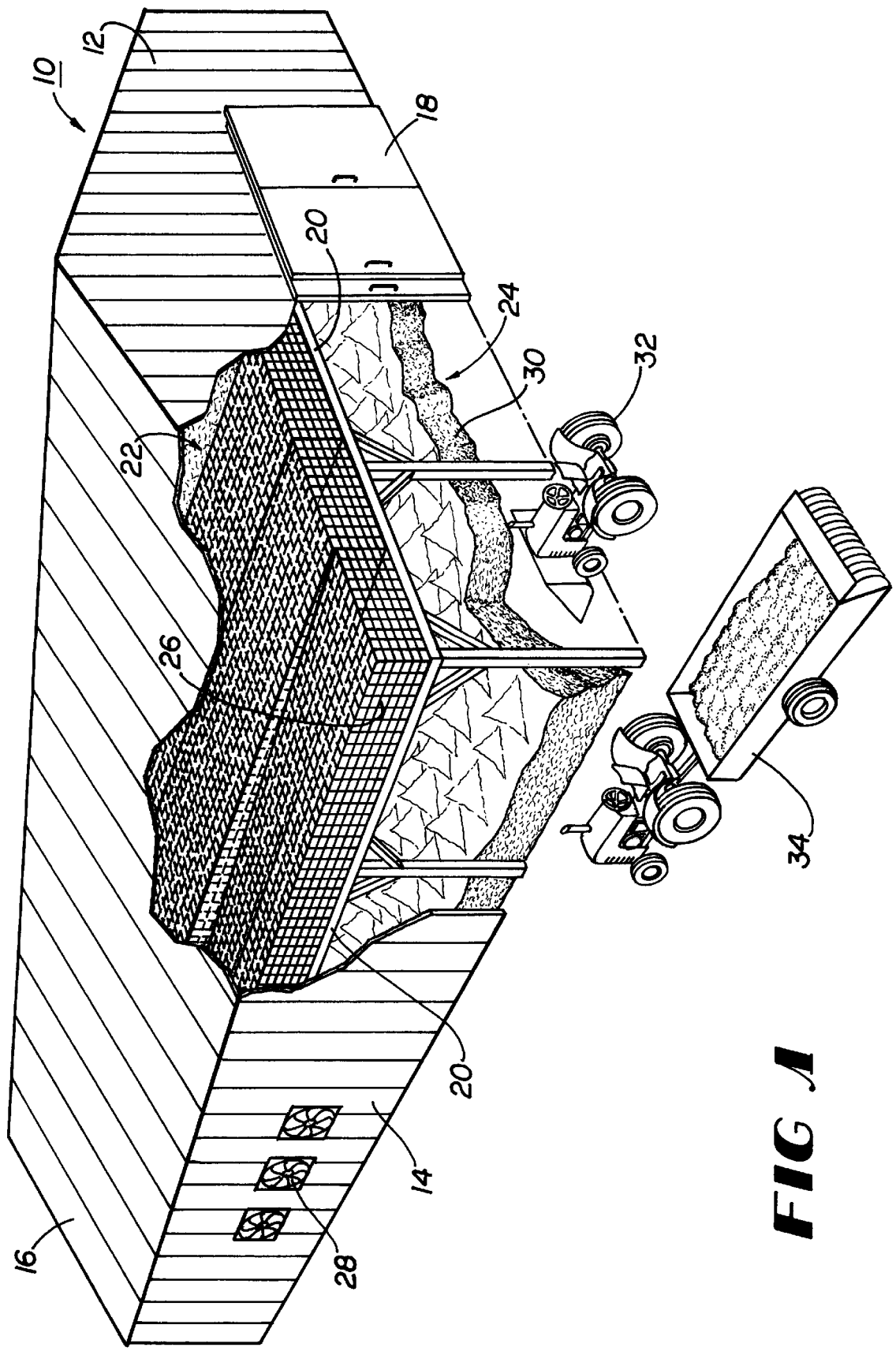
FIG. 1 is a perspective view of a high-rise animal rearing facility in accordance with the present invention partially cut away to show the animal rearing level and manure collection level.

Referring now to FIG. 1, a animal rearing facility in accordance with an embodiment of this invention is generally referred to by reference numeral 10. In a preferred embodiment, rearing facility 10 comprises a high-rise rearing facility for commercial production of laying hens.

Figure 2:
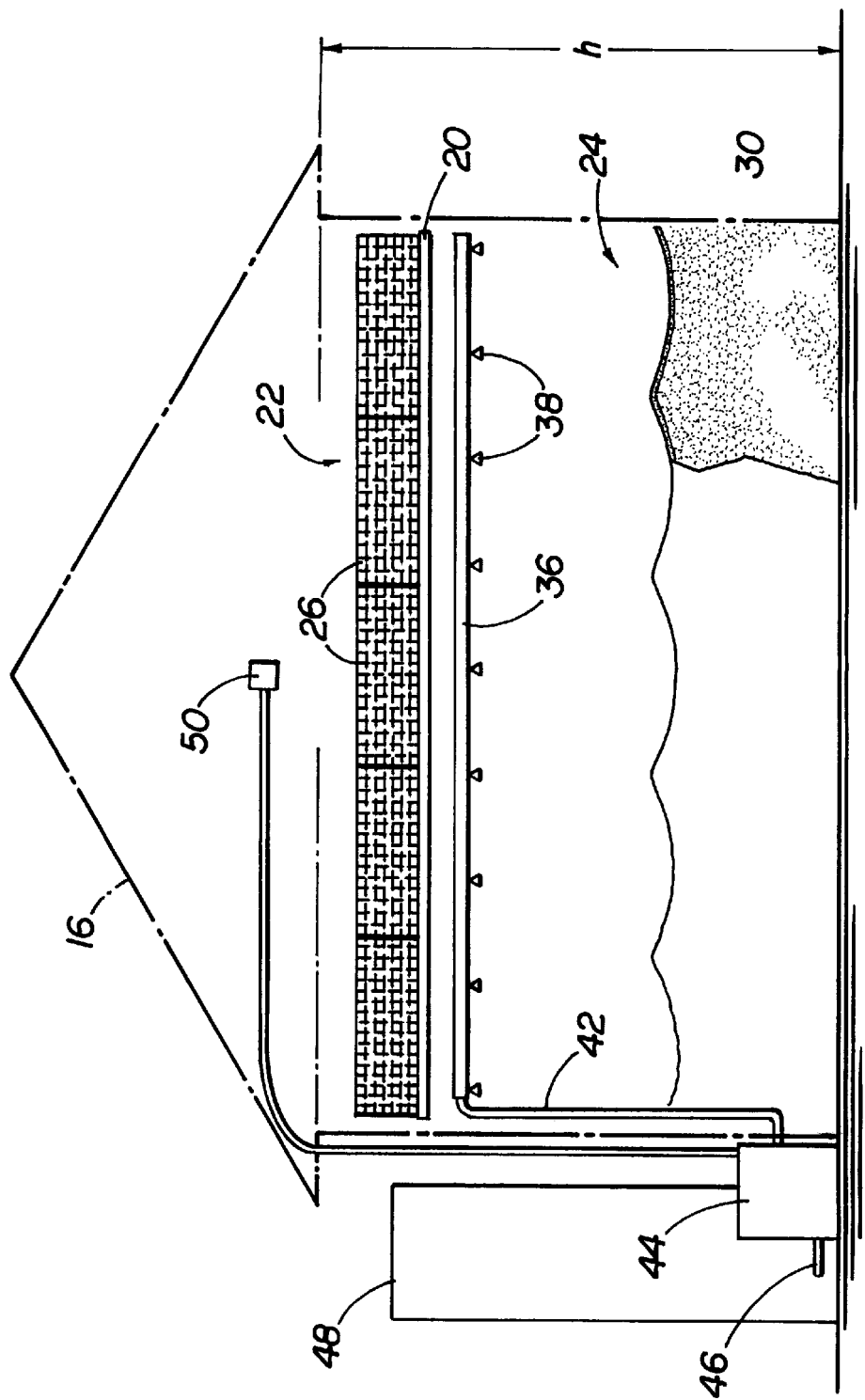
FIG. 2 is a partly schematic side elevation view of a high-rise animal rearing facility in accordance with the present invention.

Rearing facility 10 includes an enclosure having a generally rectangular configuration bounded by a plurality of upstanding peripheral sidewalls, such as 12 and 14, and a roof 16. As shown in FIG. 2, the upstanding sidewalls define a height dimension, h, for rearing facility 10. Preferably, a plurality of large bay doors 18 are provided in sidewall 12. A raised animal rearing platform 20 is provided in the enclosure which effectively subdivides the enclosure to define an upper animal rearing area 22 above platform 20 and a manure collection area 24 below platform 20 and animal rearing area 22. In accordance with the preferred embodiment depicted in FIG. 1, a plurality of cages 26 are provided on platform 20 to house each successive generation of laying hens raised in the facility. Preferably, a plurality of exhaust or ventilation fans 28 may be provided in sidewall 14.

Raised platform 20 includes a plurality of openings defined therein to permit manure 30 produced by the birds in rearing area 22 to fall and accumulate in manure collection area 24. Raised platform 20 may comprise any load bearing structure having sufficient openings to permit the manure to fall and collect in the manure collection area 24 so that manure does not accumulate significantly in the animal rearing area 22. Platform 20 preferably comprises wire mesh, although a punched metal sheet, or a plurality of spaced metal or wood slats may also be used. Platform 20 is preferably positioned at a vertical height which is high enough to provide access to the manure collection area 24 by mechanized removal equipment, such as a bulldozer or shovel tractor 32. Tractor 32 scoops manure 30 out of collection area 24 and loads it into a manure spreader 34 for application to the land as an agricultural fertilizer.

Referring now to FIG. 2, new and improved animal rearing facility 10 further comprises a liquid chemical treatment delivery system for periodically applying a liquid chemical treatment to the manure collection area to provide improved atmospheric conditions in the animal rearing area 22.

Figure 3:
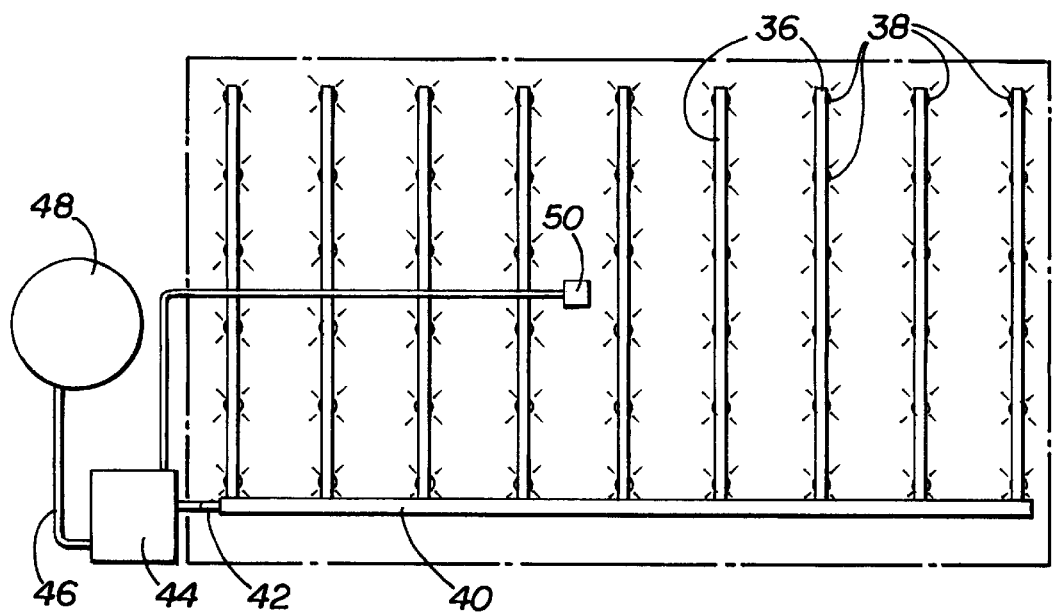
FIG. 3 is a schematic top plan view of a liquid alum treatment delivery system in accordance with this invention employing stationary nozzles in accordance with a first embodiment.

More particularly, in the preferred embodiments shown in FIGS. 2–3, the delivery system comprises a plurality of spaced apart sprayer wands 36 mounted adjacent an underside surface of raised platform 20 in the manure collection area 24. Each wand 36 includes a plurality of mister or sprayer nozzles 38. Each of wands 36 are fluidly connected at one end to a fluid flow manifold 40 which in turn is fluidly connected by a fluid flow conduit 42 to the output or discharge side of a fluid pump 44. The input side of pump 44 is fluidly connected by conduit 46 to a liquid chemical treatment supply tank 48. In the preferred embodiment shown in FIGS. 2–3, an ammonia sensor 50 is provided in the animal rearing area 22 for sensing the concentration of ammonia present in the atmosphere of the animal rearing area 22. Ammonia sensor 50 is operable to send a control signal to the pump operation control whenever the concentration of ammonia in the animal rearing area 22 reaches or exceeds 25 ppm.

Pump 44 may comprise any fluid delivery pump useful for pumping fluids, such as a manual pump, a vane pump, solenoid pump, diaphragm metering pump, or the like. Preferably, pump 44 is an electronically controlled metering pump capable of adjustably delivering known quantities of fluid from supply 48 to nozzles 38. The pump control preferably permits the pump to be programmed to turn on at adjustable intervals of time for adjustable duration on times to deliver desired quantities of liquid chemical treatment to the manure collection area. The pump may be interactively controlled by the ammonia sensor output to turn on the pump to apply liquid chemical treatment of a certain volume over a certain period of time, or alternatively, the sensor may be programmed to turn on the pump when ammonia levels exceed 25 ppm and to stay on until the ammonia level falls to a specified lower limit such as 20 ppm or 15 ppm, whereupon the sensor signals the pump controller to turn the pump off again. In this manner, spray application of the liquid chemical treatment may proceed in accordance with a programmed time schedule, with or without an ammonia sensor control override, or may proceed under a manual control on an as-needed basis as determined by the ammonia sensor sensing actual atmospheric ammonia conditions in the animal rearing area 22.

The pump 44 is capable of delivering the liquid chemical, in particular liquid alum, treatment to the sprayer or mister nozzles 38 under pressure and pressures of between about 1 to about 50 psi are usually sufficient. Nozzles 38 should be of the type capable of delivering the liquid alum in finely divided droplet form, and mistforming nozzles are preferred, although other spray nozzles may be used. Means for inhibiting clogging such as brief periodic flushing of the nozzles with fresh water or air may be incorporated.

Figure 4:
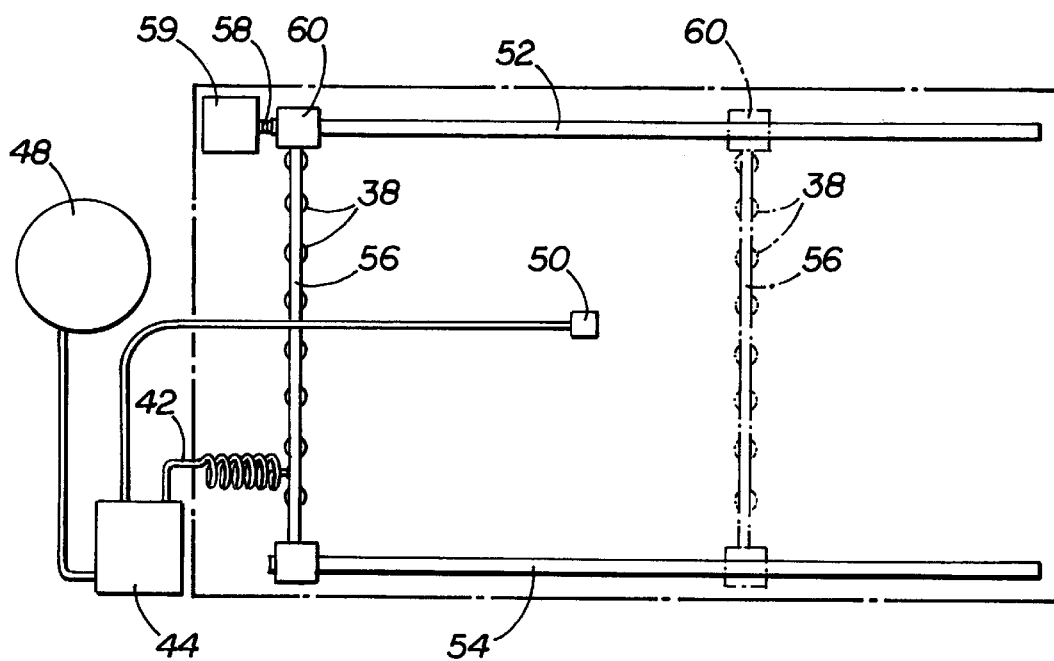
FIG. 4 is a schematic plan view of the liquid chemical treatment delivery system in accordance with an alternate embodiment of the invention in which a movable nozzle system is employed.

Referring now to FIG. 4 an alternate embodiment of a liquid alum delivery system is shown employing a movable mounted nozzle array for applying the liquid alum over substantially the entire surface of the manure present in the manure collection area 24. In accordance with this embodiment, a pair of guide rails 52 and 54 are mounted in the manure collection area 24 adjacent the underside surface of platform 20. A manifold 56 provided with a plurality of sprayer nozzles 38 is movably mounted to and extends between rails 52 and 54. Guide rail 52 houses a rotatably mounted worm shaft 58 which is rotatably driven by drive motor 59. One end of manifold 56 includes a worm gear 60 which is threadably engaged on worm shaft 58. Rotation of worm shaft 58 is effective to cause reciprocal or bi-directional translation of manifold 56 along the length of guide rails 52 and 54. Manifold 56 is fluidly connected by conduit 42 to the output discharge of a fluid pump 44. Operation of worm drive motor 59 is preferably under cooperative interactive control of the pump operation control, so that the translation rate of the manifold 56 may be coordinated with the pump flow rate to evenly apply the liquid chemical treatment to the surface of the manure accumulated in the manure collection area.

In accordance with the present invention, the application of aluminum sulfate (alum) onto the manure lowers the pH of the manure, converting ammonia generated by the manure to ammonium which combines with sulfate to form ammonium sulfate which is a water soluble nitrogen fertilizer. This process increases the fertilizer value of the manure and simultaneously improves the atmosphere inside the animal rearing facility for both animals and humans alike.

A method of applying the alum to manure in a high-rise laying hen house is to spray it from a system such as that shown in FIGS. 2–4. In a system of this kind, a solution of aluminum sulfate is pumped from a holding tank or other receptacle through suitable piping made of non-corroding material such as PVC or other plastic piping to sprayers or nozzles which form a mist. The sprayers or nozzles should also be constructed of corrosion resistant materials. Fogging systems such as those used to cool animal rearing facilities are generally suitable and may be used for this purpose.

The alum solution should be sprayed onto the manure periodically as needed to lower atmospheric ammonia levels suitable for maximizing animal husbandry. For laying hens, this level is approximately 25 ppm $NH_3$ or less.

The periodicity of the alum applications may be controlled in a number of ways including: by using a timing device to activate the sprayers, by using an ammonia sensing device to activate the sprayers at predetermined ammonia concentrations, and/or by manual controls wherein the operator may turn on the liquid chemical treatment spraying system as necessary as determined by the operators nose.

The aluminum sulfate concentration in the alum solution may be varied from approximately 1 to about 50% by weight, however the most commonly used solution contains about 48.5% by weight aluminum sulfate in water. This is equivalent to 5.4 lbs. of dry alum per U.S. gallon.

One of several different techniques might be used to prevent clogging of the spraying equipment. These may include diluting the alum solution with water and flushing the pipes and spray equipment with either water or air after each alum application. The necessary structures for accomplishing line flushing will be readily apparent to those skilled in this art.

The liquid chemical treatment delivery system may be a moving system such as that shown in FIG. 4 or a non-moving spray system such as that shown in FIGS. 2–3. In a moving delivery system, the spraying equipment moves up and down or back and forth the length of the house on tracks, chains, wires or some other type of conveying or pulley system. In non-moving systems, spraying equipment of adequate scope is provided to afford ample coverage. The equipment remains stationary and is arranged in such manner that the spray covers most of the manure area in the house.

The amount of alum sprayed on the manure will depend on the number of animals in the house and the subsequent amount of manure generated, and such that the alum will control the ammonia volatilization. Although the liquid alum is sprayed or otherwise applied in relatively small quantities daily or weekly, the cumulative amount of alum delivered in this system preferably should be such as to result in a mixture which contains 25–250 g of $Al_2(SO_4)_3 \cdot 14H_2O$ per kg of manure (on a dry weight basis), with the preferred application rate resulting in approximately 100 g of $Al_2(SO_4)_3 \cdot 14H_2O$ per kg of manure (equivalent to approximately 10% alum by weight).

It should be noted that laying hens and brood poultry, for example, are not raised on bedding materials or any sort of material which would be referred to as litter that would be adversely impacted if additional moisture were introduced thereto. Hence, this method does not entail addition of alum to animal bedding or litter, but rather describes a condition where the alum is applied directly to the manure, removed from the animals and where the physical state of the manure may vary from a dry solid composed of mainly manure to a liquid slurry which may have more water than manure.

By way of illustration, a high-rise laying hen house may contain approximately 50,000 laying hens of a breed which produces about 15 lbs. of manure on a dry weight basis per bird per year. Accordingly, in this facility there would be 750,000 lbs. (375 tons) of manure generated annually. The amount of alum needed to be applied to control the atmospheric conditions of the rearing facility would be approximately 37.5 tons of $Al_2(SO_4)_3 \cdot 14H_2O$ per house per year, or about 13,900 gallons of liquid alum (48.5% by weight alum solution). This would be equivalent to 267 gallons of liquid alum per week or 38 gallons of alum per day.

The above illustration will lead those skilled in the art to determine the quantity of liquid alum which needs to be supplied to the manure collection area to control ammonia volatilization and improve the rearing conditions for the animals raised in the facility. The 38 gallons of alum per day in the commercial high-rise laying hen house may be applied at a rate of approximately 1.5 gallons per hour through the misters which may run continuously or intermittently as desired. Those skilled in the art, without undue experimentation, will be able to calculate the relative amounts of alum which will be required for smaller facilities.

It should be noted that the above illustration is provided for general guidance and that many different factors can influence the amount of alum needed to properly reduce ammonia volatilization. Accordingly, actual amounts delivered daily or weekly may vary. Some of the factors which influence the amount of alum which might be needed include the type of animal, the breed of animal, the numbers of animals and the diet of the animal. More particularly, the amount of alum needed to lower the manure pH sufficient to reduce ammonia volatilization will generally increase as the amount of $CaCO_3$ in the diet of the animals increases or vice-versa.

Another major factor affecting the amount of alum required to decrease volatilization of ammonia is the moisture content of the manure. In general, it may be stated that the amount of alum needed will increase as the moisture content increases.

Although the present invention has been described with reference to certain preferred embodiments, modifications or changes may be made therein by those skilled in this art. For example, the liquid chemical treatment may be delivered to the spraying system in a gravity feed system wherein the liquid chemical supply tank is mounted on or above the roof of the enclosure and fed by a conduit to the sprayer nozzles. A valve may be disposed in the conduit line to maintain the flow of liquid chemical treatment in a normally off position, which may be opened manually or automatically from time to time as needed or desired to permit the liquid chemical to flow under the influence of gravity from the storage tank to the sprayer nozzles under pressure.

Other movably mounted nozzle arrangements will suggest themselves to those skilled in this art. For example, instead of a single movably mounted manifold movable in a single axis direction, a mounting arrangement for a nozzle may be provided which is movable in x and y axes to manipulate or move the nozzle so that it can spray and cover the entire surface area of the manure collection area. Although the preferred liquid chemical treatment utilized by the invention comprises a liquid alum solution, other liquid chemical treatments found to be effective at controlling ammonia volatilization, such as urease inhibitors, as well as, supplemental additives, such as a disinfectant, might also be included in the liquid chemical delivery system in accordance with the present invention. Although a high-rise laying hen growing facility is described in connection with the preferred embodiments, other animals such as dairy cows or swine, may also be grown in high-rise rearing facilities which may be modified in accordance with the teachings and principles of this invention to provide improved animal rearing facilities for these animals. "High-rise" being inclusive of a facility in which the animal manure falls away from the level on which the animal is housed to a level below. All such obvious modifications or changes may be made herein by those skilled in this art, without departing from the scope or spirit of the present invention, as defined by the appended claims.

What is claimed is:

1. A method for improving atmospheric conditions in a high-rise animal rearing facility, wherein animals are reared in an enclosure on an animal rearing level on a raised platform and manure from the animals falls to a manure collection level disposed below the raised platform, said method comprising:

spraying an aluminum sulfate solution onto an upper surface of manure present in the manure collection level in amounts and at spraying intervals which are effective to maintain a pH of the surface of the manure at less than or equal to about 7.0 and which are effective to control the atmospheric concentration of ammonia in the animal rearing level at less than or equal to about 25 ppm.

2. A method for improving atmospheric conditions in a high-rise animal rearing facility at as defined in claim 1, wherein the concentration of the alum solution sprayed is from about 1% to about 50% by weight.

3. A method for reducing odors associated with a high-rise animal rearing facility, wherein animals are reared in an enclosure on an animal rearing level on a raised platform and manure from the animals falls to a manure collection level disposed below the raised platform, said method comprising:

spraying an aluminum sulfate solution onto an upper surface of manure present in the manure collection level in amounts and at spraying intervals which are effective to maintain a pH of the surface of the manure at less than or equal to about 7.0 and which are effective to control the atmospheric concentration of ammonia in the animal rearing level at less than or equal to about 25 ppm.

4. A method for reducing odors associated with a high-rise animal rearing facility as defined in claim 3, wherein the concentration of the alum solution sprayed is from about 1% to about 50% by weight.

5. A method for reducing acid rain and $PM_{10}$s associated with atmospheric ammonia pollution originating from a high-rise animal rearing facility, wherein animals are reared in an enclosure on an animal rearing level on a raised platform and manure from the animals falls to a manure collection level disposed below the raised platform, said method comprising:

spraying an aluminum sulfate solution onto an upper surface of manure present in the manure collection level in amounts and at spraying intervals which are effective to maintain a pH of the surface of the manure at less than or equal to about 7.0 and which are effective to control the atmospheric concentration of ammonia in the animal rearing level at less than or equal to about 25 ppm.

6. A method for reducing acid rain and $PM_{10}$s associated with atmospheric ammonia pollution originating from a high-rise animal rearing facility as defined in claim 5, wherein the concentration of the alum solution sprayed is from about 1% to about 50% by weight.

7. A method for reducing phosphorus solubility of and non-point source phosphorus pollution arising from poultry manure fertilizers obtained from a high-rise animal rearing facility, wherein animals are reared in an enclosure on an animal rearing level on a raised platform and manure from the animals falls to a manure collection level disposed below the raised platform, said method comprising:

spraying an aluminum sulfate solution onto an upper surface of manure present in the manure collection level in amounts and at spraying intervals which are effective to maintain a pH of the surface of the manure at less than or equal to about 7.0 and which are effective to control the atmospheric concentration of ammonia in the animal rearing level at less than or equal to about 25 ppm.

8. A method for reducing phosphorus solubility of and non-point source phosphorus pollution arising from poultry manure fertilizers obtained from a high-rise animal rearing facility as defined in claim 7, wherein the concentration of the alum solution sprayed is from about 1% to about 50% by weight.

* * * * *